United States Patent
Haywood

(10) Patent No.: US 6,988,893 B2
(45) Date of Patent: Jan. 24, 2006

(54) DISPOSABLE PHOTOGRAPHIC CHEEK RETRACTION APPARATUS AND METHOD OF USING THE SAME

(75) Inventor: Van Benjamine Haywood, Martinez, GA (US)

(73) Assignee: Medical College of Georgia Research Institute Inc., Augusta, GA (US)

( * ) Notice: Subject to any disclaimer, the term of this patent is extended or adjusted under 35 U.S.C. 154(b) by 347 days.

(21) Appl. No.: 10/243,819

(22) Filed: Sep. 13, 2002

(65) Prior Publication Data

US 2004/0053193 A1 Mar. 18, 2004

(51) Int. Cl.
*A61C 5/00* (2006.01)

(52) U.S. Cl. .................. 433/140; 600/242
(58) Field of Classification Search .......... 433/140; 128/859; 600/242, 210, 217, 235, 243, 237; 211/119
See application file for complete search history.

(56) References Cited

U.S. PATENT DOCUMENTS

| | | | |
|---|---|---|---|
| 776,302 A * | 11/1904 | Crockett | 600/242 |
| 1,813,650 A * | 7/1931 | Whitlock | 433/138 |
| 3,735,491 A | 5/1973 | Pabalan | |
| 4,889,490 A * | 12/1989 | Jenkinson | 433/136 |
| 5,115,799 A * | 5/1992 | McGann | 600/242 |
| 5,514,076 A * | 5/1996 | Ley | 600/206 |
| 5,558,622 A * | 9/1996 | Greenberg | 600/237 |
| 5,873,718 A | 2/1999 | Sullivan | |
| 5,897,492 A * | 4/1999 | Feller et al. | 600/240 |
| 6,102,701 A * | 8/2000 | Engeron | 433/140 |
| 6,273,280 B1 * | 8/2001 | Markarian | 211/113 |
| 6,338,627 B2 | 1/2002 | Hirsch et al. | |
| 6,413,231 B1 * | 7/2002 | Berman et al. | 601/38 |

\* cited by examiner

Primary Examiner—John J Wilson
(74) Attorney, Agent, or Firm—Technology Legal Counsel LLC

(57) ABSTRACT

In an exemplary embodiment in accordance with the present invention, a disposable dental appliance and method of use is provided. In particular, a cheek retraction apparatus is provided, which is formed from a lightweight yet durable biocompatible polymer. The apparatus is sufficiently durable to withstand recurrent use, however, the it is economically manufactured so as to be disposable. Moreover, the apparatus is pre-sterilized to alleviate the need for autoclaving and/or dry heat sterilization. A cheek retraction apparatus in accordance with the present invention also provides an indicia display medium that allows the dental practitioner to display patient information, whitening treatment measurements, or other indicia that might be useful to them during oral photography.

14 Claims, 6 Drawing Sheets

DISPOSABLE PHOTOGRAPHIC CHEEK RETRACTION APPARATUS AND METHOD OF USING THE SAME

FIELD OF THE INVENTION

The present invention relates generally to medical devices and a disposable dental appliance for intra-oral cheek retraction and photography in particular.

BACKGROUND OF THE INVENTION

Dentists regularly have to strike an unsatisfactory compromise between patient comfort and work area accessibility. In particular, in order to achieve increased visibility and access to intra-oral work areas, patients have to endure some level of discomfort. In order to address this problem, practitioners have attempted to design devices that help guide patients into maximum intercuspation (MI) while decreasing working time in hard to reach areas. However, many of these devices are made of metal, which can be expensive and could cause tissue damage to patients. Moreover, particular attention must be given when autoclaving such devices.

Limitations of metal devices inspired dentists to design the next generation of devices, which are made of autoclavable polymers such as plastic. These devices address many of the limitations of metal, however, they still remain relatively expensive to produce and still require autoclaving and dry heat sterilization. Additionally, when conducting oral photography for purposes of comparing x-rays or tooth whitening treatments, an additional appliance must be used to provide descriptive information about the patient and/or procedure being photographed.

Therefore, there is an existing need for a dental appliance that strikes the proper balance between patient comfort and work area accessibility. Additionally, a dental appliance that is manufactured from a biocompatible polymer is desirable. More particularly, it is preferable that the biocompatible polymer is an extrudable plastic that lends itself to economical mass production. Moreover, there is an existing need for a disposable dental appliance that is pre-sterilized to obviate the need for autoclaving or dry heat sterilization. Additionally, there remains an existing need for a dental appliance that provides for the presentation of clinical information in addition to its functionality as an oral workspace-maximizing device.

SUMMARY OF EXEMPLARY EMBODIMENTS

The present inventor has discovered a unique way of addressing all of the above limitations and providing additional advantages. In an exemplary embodiment in accordance with the present invention, a disposable dental appliance and method of use is provided. In particular, a cheek retraction apparatus is provided, which is formed from a lightweight, yet durable, biocompatible polymer. The cheek retraction apparatus is sufficiently durable to withstand recurrent use; however, the retraction apparatus is economically manufactured so as to be disposable. Moreover, the cheek retraction apparatus is pre-sterilized to alleviate the need for autoclaving and/or dry heat sterilization. A cheek retraction apparatus in accordance with the present invention also provides an indicia display medium that allows the dental practitioner to display patient information, whitening treatment measurements, or other indicia that might be useful to them during oral photography.

In a preferred embodiment, it is an objective of the invention to provide a disposable dental appliance that can be easily placed, removed and replaced, preferably, in a patient's mouth to increase oral workspace without material discomfort to the patient. In the furtherance of this and other objectives, a polymer cheek retraction apparatus is provided that is durable yet lightweight. Moreover, when used, the appliance adequately cradles the cheek so as to reduce muscle fatigue while maximizing the oral work area for the dental practitioner.

A principal objective of the present invention is to provide a dental appliance that can be economically manufactured. In the furtherance of this and other objectives, a cheek retraction apparatus is preferably extruded from a lightweight plastic. In alternative embodiments, the apparatus may be formed from a biocompatible polymer into a single extrusion product or may be assembled by the user from several individual components. In the latter instance, a template is provided which comprises multiple pieces of the appliance; the pieces can be removed from the template and assembled by the end user by snapping the components into place.

As an adjunct to the previous objective, a preferred embodiment of the present invention provides a dental appliance that can be manufactured in sufficient quantities and at such an economical price that it is preferable to indicate the appliance as a single-use disposable appliance.

Still another objective of the present invention is to provide an alternative to the current systems that require autoclaving and dry heating, which have inherent disadvantages and contributes to the obsolescence of the device. In the furtherance of this and other objectives, a cheek retraction apparatus, in accordance with a preferred embodiment, is provided that is pre-sterilized, making autoclaving and/or dry heat sterilization unnecessary. In particular, the cheek retraction apparatus in accordance with the present invention undergoes a sterilization treatment prior to being packaged.

A principal objective of a preferred embodiment of the present invention is to provide a dental appliance useful during oral photography. In the furtherance of this and other objectives, a preferred appliance comprises an indicia retainer for displaying clinical information related to the patient, such as the patient's contact information, customer identification number or before-and-after tooth whitening treatment comparison information. A wide range of indicia, useful to the dental practitioner, may be coupled with the dental appliance and displayed.

Further objectives, features and advantages of the invention will be apparent from the following detailed description taken in conjunction with the accompanying drawings.

DETAILED DESCRIPTION OF THE PREFERRED EMBODIMENTS

The present invention provides a cheek retraction apparatus. In an exemplary embodiment in accordance with the present invention, a disposable dental appliance and method of use is provided. In particular, a cheek retraction apparatus is provided, which is formed from a lightweight yet durable biocompatible polymer. The dental appliance is sufficiently durable to withstand recurrent use, however, the appliance is economically manufactured so as to be disposable. Moreover, the appliance is pre-sterilized to alleviate the need for autoclaving and/or dry heat sterilization. A dental appliance in accordance with the present invention also provides an indicia display medium that allows the dental practitioner to display patient information, whitening treatment measurements, or other indicia that might be useful to them during oral photography.

Figure 1:
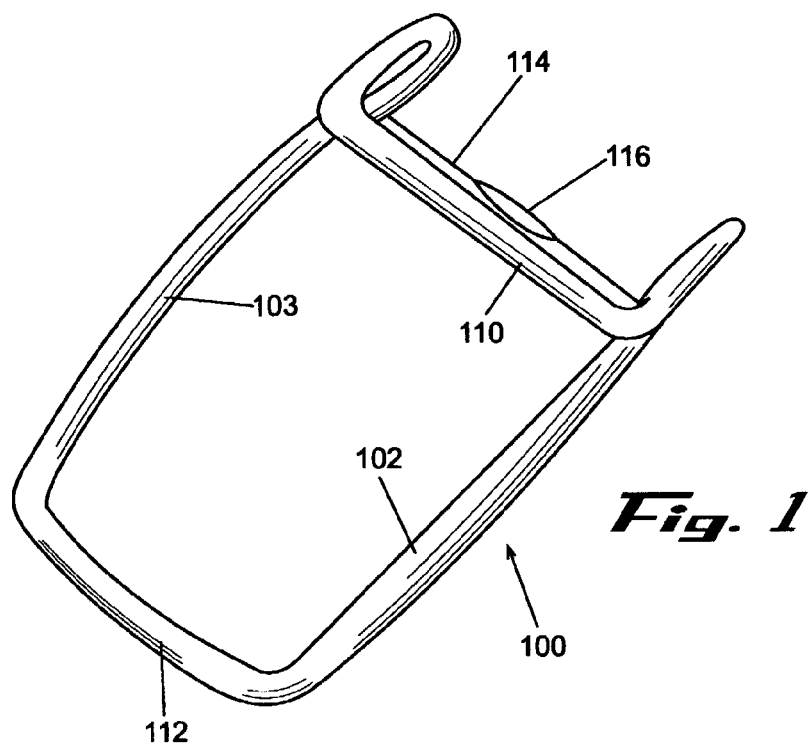
FIG. 1 is a rear perspective view of a cheek retraction apparatus embodying the present invention.

Referring now to the figures, where like numbers refer to like parts, the dental appliance comprises a substantially hook shaped configuration for enhanced stability and patient comfort. In a preferred embodiment, as shown in FIG. 1, the dental appliance comprises a completely integrated cheek retraction apparatus 100 formed from a biocompatible polymer having support members 102 & 103 that longitudinally extend substantially parallel with respect to one another and coupled together at their working and non-working ends by perpendicularly extending connection members 110 & 112, respectively.

In this embodiment, the support members 102 & 103 and the connection members 110 & 112 connect end to end to form a substantially continuous loop. In a preferred embodiment, an additional connection member 114 is provided that connects at each end with support members 102 & 103 between the working and non-working ends of the cheek retraction apparatus 100. Connection member 114 preferably defines an aperture 116 (hereinafter referred to as "indicia retainer") disposed along the longitudinal expanse thereof, for receiving and retaining an indicia display medium (not shown in this figure) for displaying clinically desirable patient information. The indicia display medium is disposed between support members 102 & 103 through connection member 114. In alternative embodiments, the indicia display medium can be disposed through apertures formed on other suitable portions of the cheek retraction apparatus 100. Non-limiting examples of such locations would be on other connection members or portions of the support members.

Figure 6:
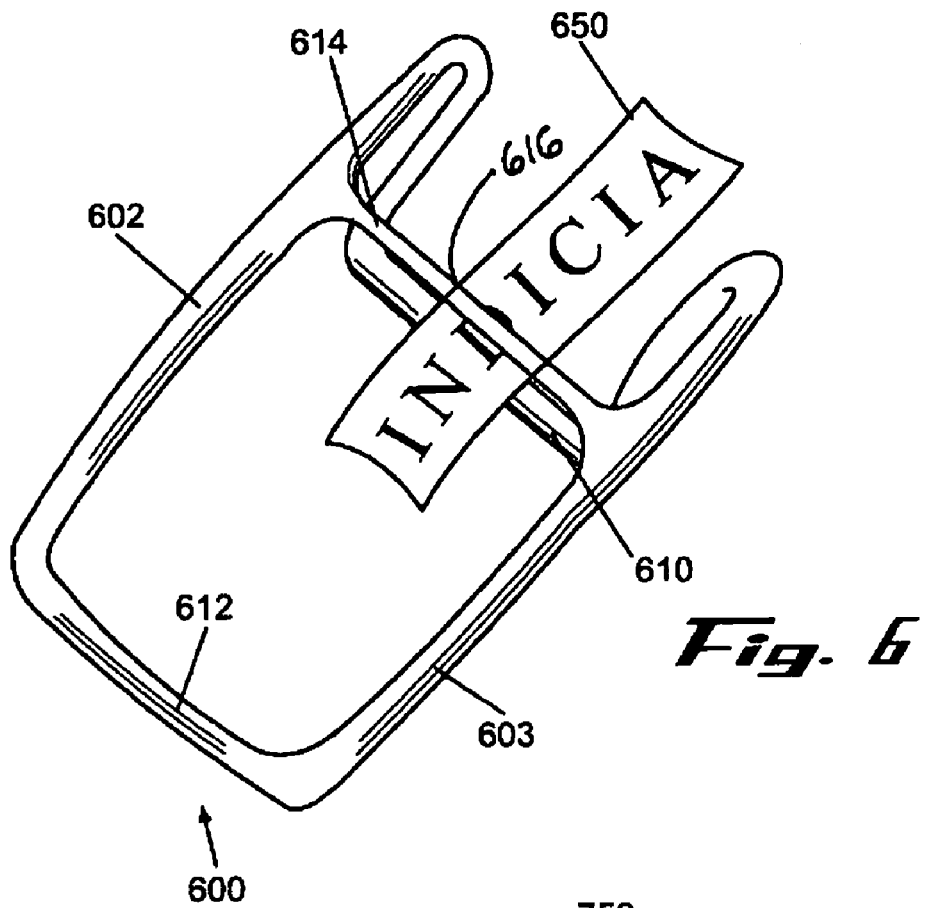
FIG. 6 is a front perspective view of an alternative embodiment of the cheek retraction apparatus, in accordance with the present invention, showing the indicia-display medium coupled with the cheek retraction apparatus of FIG. 1.

In practice, the user will hold a portion of connection member 112 and place a portion of connecting member 110 and support members 102 & 103 into the oral cavity of a patient. By pulling on the connection member 112, the user is able to retract the patient's cheek. This illustration, is in no way to be construed as limiting, in that the user may grasp just about any portion of the cheek retraction apparatus 100 short of the working ends of support members 102 & 103. In an exemplary embodiment, in accordance with the present invention, as shown in FIG. 6, the cheek retraction apparatus 600 is configured with an indicia retainer 616 for receiving an indicia display medium 650. The indicia display medium 650 conveniently displays clinically desirable patient information. By way of example, and by no means to be construed as limiting, the indicia to be displayed may include patient contact information, identification data, tooth whitening comparison data, time or date stamps etc. It is preferable that the indicia display medium is waterproof in the event of contact with the patient's tongue or other sources of moisture in a patient's mouth.

Figure 2:
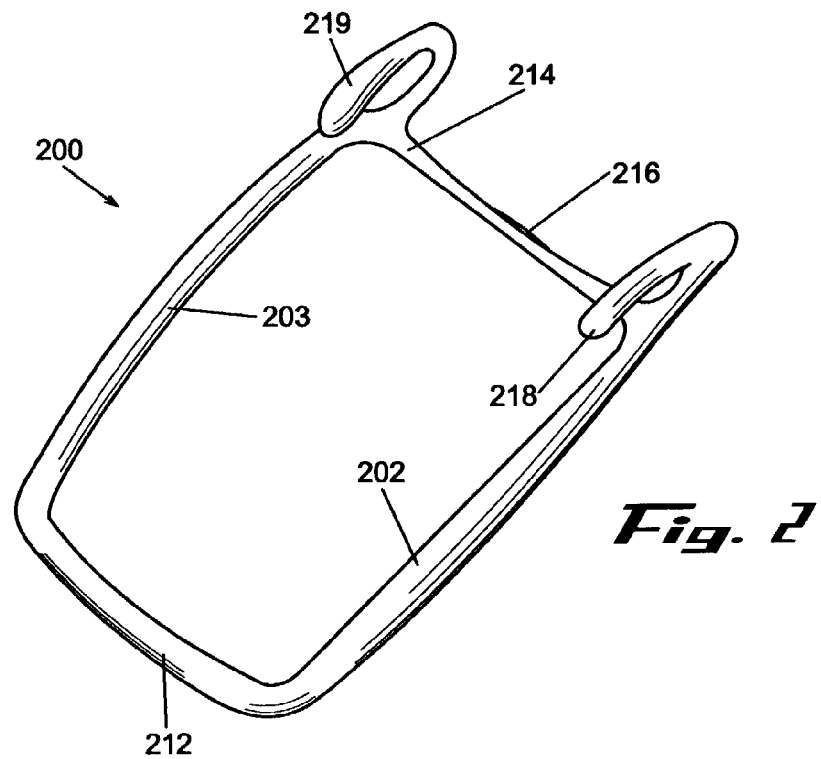
FIG. 2 is a rear perspective view of an alternative embodiment of a cheek retraction apparatus embodying the present invention.
Figure 7:
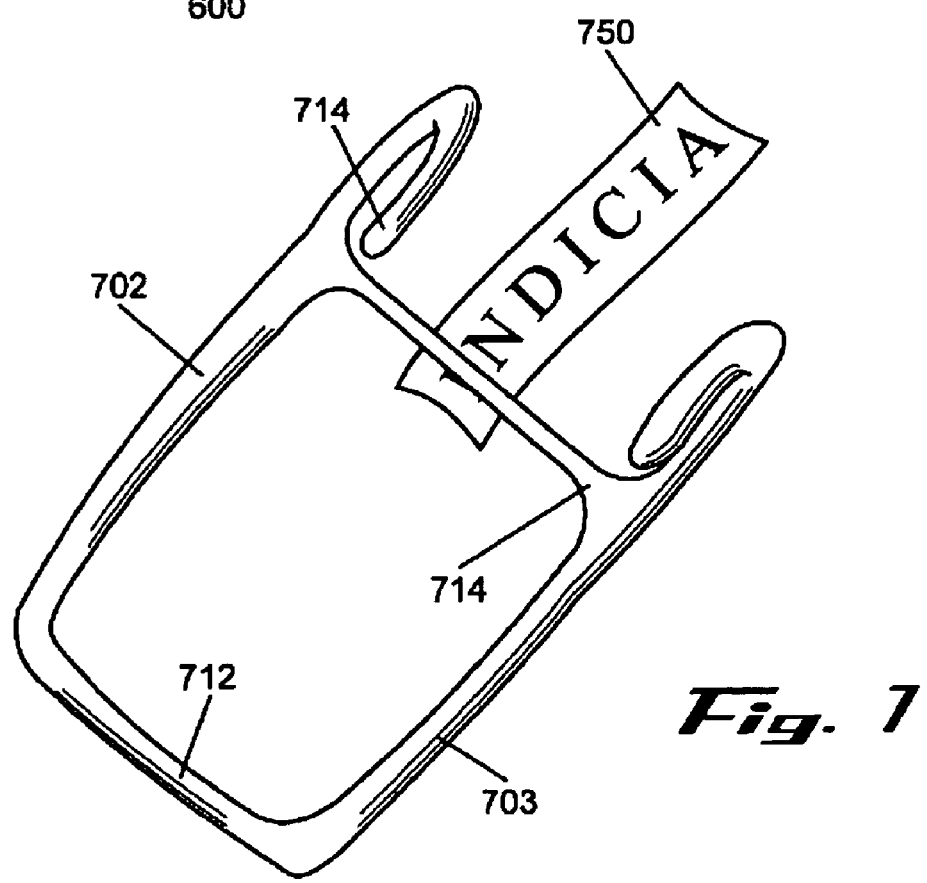
FIG. 7 is a front perspective view of an alternative embodiment of the cheek retraction apparatus, in accordance with the present invention, showing the indicia-display medium coupled with the cheek retraction apparatus of FIG. 2.

Referring now to FIG. 2, an alternative embodiment is provided that allows for cheek retraction via certain pressure points at the working ends of support members 202 & 230 of cheek retraction apparatus 200 rather than use of an equivalent to the connection member 110 of cheek retraction apparatus 200. FIG. 7 shows a similar embodiment having an indicia display medium 750.

Figure 3:
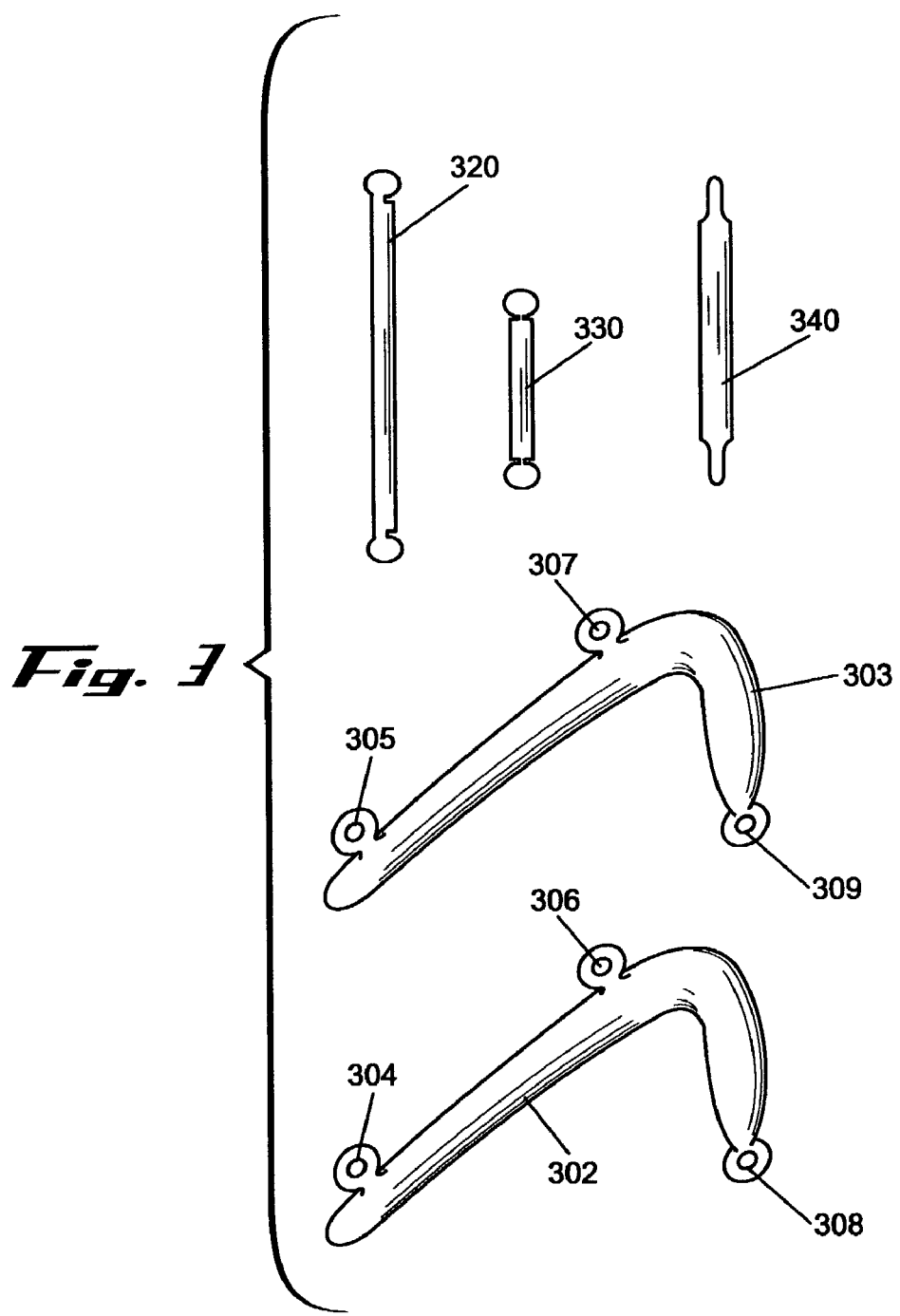
FIG. 3 is an exploded view of the component parts of a cheek retraction apparatus, embodying the present invention, as shown in FIG. 1.
Figure 4:
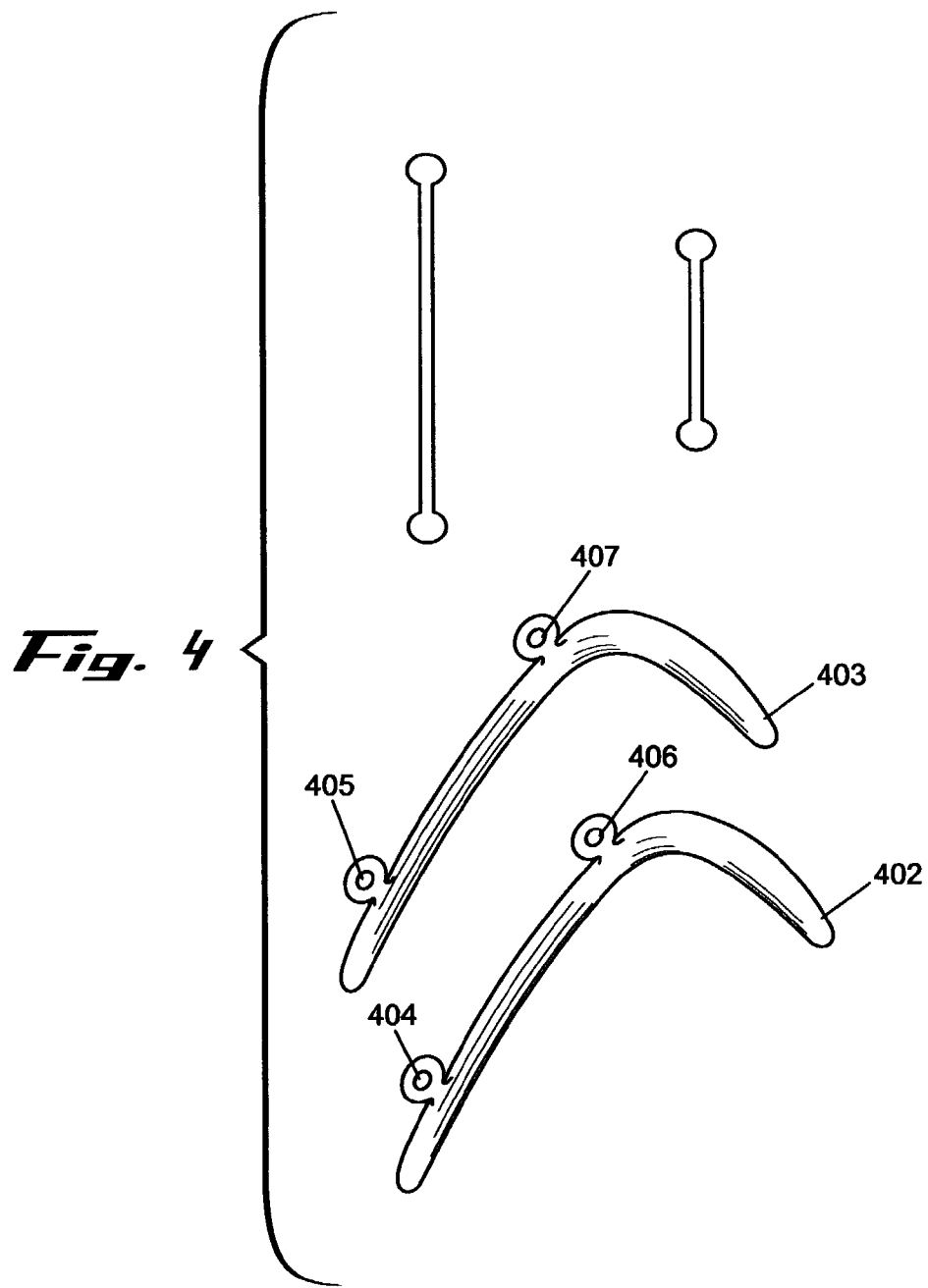
FIG. 4 is an exploded view of the component parts of a cheek retraction apparatus, embodying the present invention, as shown in FIG. 2.
Figure 8:
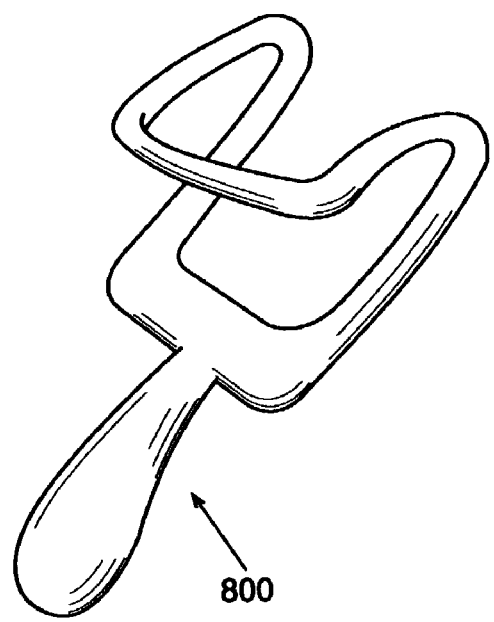
FIGS. 8 & 9 are aerial perspective views of alternative embodiments of the cheek retraction apparatus in accordance with the present invention.

As we turn to FIG. 3, it must be noted that cheek retraction apparatuses 100, 200, 600, 700 and 800 are manufactured from a biocompatible polymer, which is preferably an injection molded or extrudable plastic. In a preferred embodiment, a dental appliance as shown in FIGS. 3 & 4 can be manufactured as individual components that can be installed by the end user. In particular, a cheek retraction apparatus 300 in accordance with the closed design comprises two support members 302 & 303, which each define a plurality of apertures 304, 306, 308 and 305, 307 & 309, respectively. Apertures 304, 306 & 308 and 305, 307 & 309 are configured to receive complementary ends of connection members 320, 330 and 340 to form an integrated dental appliance as shown in FIGS. 1, 6 and 8. FIG. 4 shows a very similar cheek retraction apparatus 400, however, the working ends 419 of support members 402 & 403 of cheek retraction apparatus 400 do not terminate at or about an additional support member, as is the case with the closed embodiment. The configuration of cheek retraction apparatus 400 is referred to as the open configuration.

Figure 5:
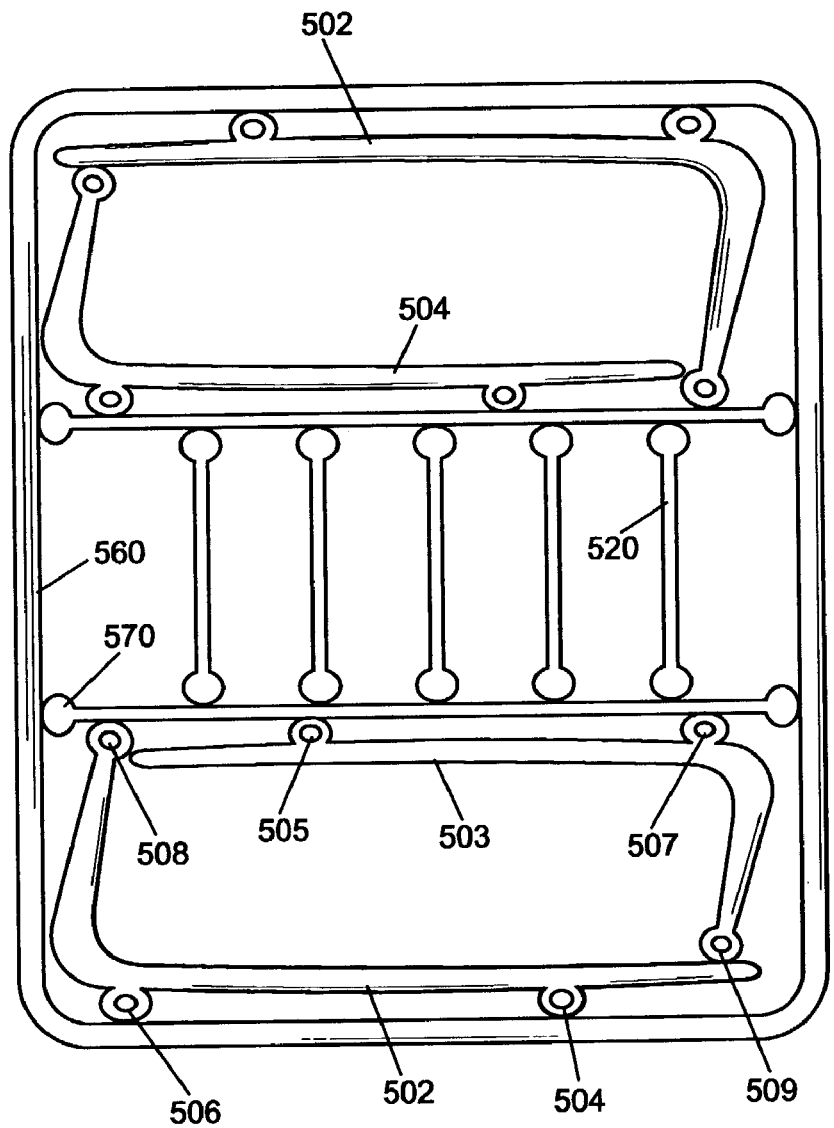
FIG. 5 is a top plan view of a template containing components of the cheek retraction apparatus as shown in FIG. 1.

Referring now to FIG. 5, an exemplary cheek retraction apparatus 500 in accordance with the present invention is shown in an unassembled state. A template 560 is shown holding various components of the appliance in place via retaining means 570. A plurality of support members 502 & 503 are shown along with a plurality of short 530 and long 520 connecting members. The connecting members 520 & 530 and support members 502 & 503 may vary in length, diameter and total surface area, limited only by the practicality of its implementation in clinical practice.

Figure 9:
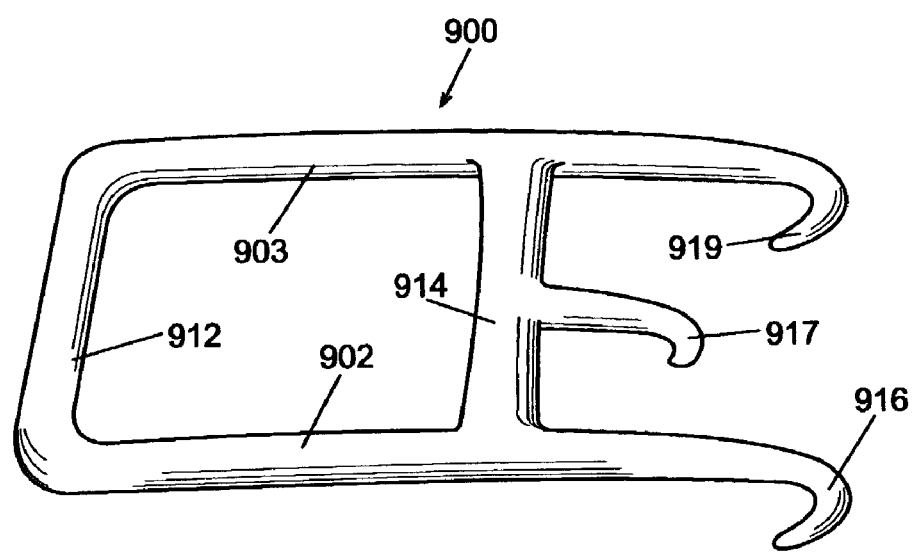

An alternative embodiment in accordance with the present invention is referred to specifically as FIG. 9. This embodiment of the cheek retraction apparatus 900 is similar to the one shown in FIG. 2. Principally, the apparatus 900 allows far cheek retraction via certain pressure points at the working ends of support members 902 & 903 of cheek refraction apparatus 900 rather than use of an equivalent to the connection member 110 of cheek retraction apparatus 100. The apparatus 900 further comprises connection members 912 & 914, however, the working ends 916 & 919 of support members 902 & 903, respectively, of cheek refraction apparatus 900 do not terminate at or about an additional support member, as is the case with closed embodiments like apparatus 100. Furthermore, there is an additional working end 917 coupled with a portion of connection member 914.

It is envisioned that all dental appliances in accordance with the present invention are pre-sterilized to prevent the need for on-site sterilization. Conventional processes for sterilizing containers that may be employed include UV irradiation, treatment with a mixture of steam and air, and an aseptic technique in which the interior wall of the container is sprayed with hydrogen peroxide and subsequently dried. Pre-sterilization methods may be selected from conventional methods within the skill of the dental appliance manufacturer and are not limited to those disclosed herein. Application may involve atomization of a liquid so that a mist is applied. After application of the disinfectant, it may be subjected to additional sprayings of hot air, if desired.

In an alternative embodiment of a dental appliance of the present invention, the support members are offset so that the apparatus slants sufficiently to cradle the area between the upper lip and lower lip of the patient. In such an embodiment, the support members may not be parallel with respect to one another. As a final note, it should be kept in mind that working and non-working ends is not strictly a reference to functionality but rather a geographical description of which end of the appliance is most likely to come into contact with the mouth of a patient (i.e., working end).

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

What is claimed is:

1. A dental appliance that facilitates the retraction of a patient's cheek when the user installs the appliance in the patient's mouth and pulls the appliance outward, the dental appliance comprising:
    a plurality of sterile support members longitudinally extending between working and non-working ends;
    a plurality of sterile connection members extending between, substantially perpendicular to and coupled with the support members to comprise a sterile dental appliance, at least one of the connection members defining an aperture there through for receiving and retaining an indicia display medium;
    whereby the user of the dental appliance grasps a portion of one of the plurality of support or connection members to direct the insertion of the working end portions of the dental appliance into the mouth of the patient in order to facilitate retraction of the cheek of the patient.

2. The dental appliance of claim 1, wherein the dental appliance is formed of a biocompatible material.

3. The dental appliance of claim 2, wherein the biocompatible material is a lightweight plastic.

4. The dental appliance of claim 1, further comprising an indicia display medium made of a water-resistant biocompatible material.

5. The dental appliance of claim 4, wherein the indicia display medium is selected from the group consisting of patient information, dental records data, date stamps, time stamps, tooth whitening indications, and combinations thereof.

6. A single-use presterilized dental appliance that facilitates the retraction of a patient's cheek when the user installs the appliance in the patient's mouth and pulls the appliance substantially horizontally outward, the dental appliance comprising:
    a plurality of support members longitudinally extending between working and non-working ends, the support members defining at least one aperture between the working and non-working ends;
    a plurality of connection members, at least one of the connection members defining an aperture there through for receiving and retaining an indicia display medium for display during oral photography, the connection members configured to engage the apertures of the support members and retain the support members in a substantially parallel orientation with respect to one another; and
    an indicia display medium threaded through and retained by the aperture of the at least one connection member;
    whereby the user of the single-use presterilized dental appliance grasps a portion of one of the plurality of support members or the at least one connection member to direct the insertion of a portion of the working end of the dental appliance into the mouth of the patient in order to facilitate retraction of the cheek of the patient.

7. The dental appliance of claim 6, wherein the dental appliance is formed of a biocompatible material.

8. The dental appliance of claim 7, wherein the biocompatible material is a lightweight plastic.

9. The dental appliance of claim 6, wherein the indicia display medium is made of a water-resistant biocompatible material.

10. The dental appliance of claim 6, wherein the indicia display medium is selected from the group consisting of patient information, dental records data, date stamps, time stamps, tooth whitening indications, and combinations thereof.

11. A method of retracting the cheek and/or lips of a patient to facilitate a dental procedure, the method comprising the steps:
    providing a sterile single-use plastic dental appliance comprising a plurality of support members longitudinally extending between working and non-working ends; a plurality of connection members extending between, substantially perpendicular to and coupled with the support members, at least one of the connection members defining an aperture there through for receiving and retaining an indicia display medium for display during oral photography;
    providing and inserting an indicia display medium through and retaining the indicia, in part, in the aperture of the sterile single-use plastic dental appliance;
    inserting a portion of the working end of the dental appliance within the oral cavity of a patient to be treated; and
    exerting a retractile force upon a portion of the dental appliance in order to facilitate retraction of a portion of the cheek and/or lip of the patient to be treated.

12. A method of photographing the teeth of a patient and providing relevant information about the patient in the photograph, without having the cheek and/or lip retraction means in the photograph, the method comprising the steps:
    providing a photographic means;
    providing a sterile single-use plastic dental appliance comprising a plurality of support members longitudinally extending between working and non-working ends; a plurality of connection members extending between, substantially perpendicular to and coupled with the support members, at least one of the connection members defining an aperture there through for receiving and retaining an indicia display medium for display during oral photography;

providing and inserting an indicia display medium through and retaining the indicia, in part, in the aperture of the sterile single-use plastic dental appliance;

inserting a portion of the working end of the dental appliance within the oral cavity of a patient to be treated;

exerting a retractile force upon a portion of the dental appliance in order to facilitate retraction of a portion of the cheek and/or lip of the patient to be treated such that the teeth and indicia are in view of the photographic means; and taking a photograph with the photographic means.

13. The method of claim 12, wherein the indicia is selected from the group consisting of patient information, dental records data, date stamps, time stomps, tooth whitening indications, and combinations thereof.

14. A single-use presterilized dental appliance that facilitates the retraction of a patient's cheek when the user installs the appliance in the patient's mouth and pulls the appliance substantially horizontally outward, the dental appliance comprising;

a plurality of support members longitudinally extending between working and non-working ends, the support members defining at least one aperture between the working and non-working ends;

a plurality of connection members, at least one of the connection members defining an aperture at least partially there through for receiving and retaining an indicia display medium for display during oral photography, the connection members configured to engage the apertures of the support members and retain the support members in a substantially parallel orientation with respect to one another; and an indicia display medium threaded through and retained by the aperture of the at least one connection member;

whereby the user of the single-use presterilized dental appliance grasps a portion of one of the plurality of support members or the at least one connection member to direct the insertion of a portion of the working end of the dental appliance into the mouth of the patient in order to facilitate retraction of the cheek of the patient.

* * * * *